US007989161B2

(12) United States Patent
Gluschankof et al.

(10) Patent No.: US 7,989,161 B2
(45) Date of Patent: Aug. 2, 2011

(54) METHODS FOR DETERMINING HUMAN IMMUNODEFICIENCY VIRUS TYPE 2 (HIV-2) PROTEASE SENSITIVITY OR RESISTANCE TO ANTIVIRALS UTILIZING AN INDUCIBLE YEAST EXPRESSION SYSTEM

(75) Inventors: Pablo Gluschankof, Marseilles (FR); Didier Raoult, Marseilles (FR); Najoua Ben M'Barek, Marseilles (FR); Gilles Audoly, Marseilles (FR)

(73) Assignees: Université de la Méditérranée (FR); Centre National de la Recherche Scientifique - CNRS (FR)

( * ) Notice: Subject to any disclaimer, the term of this patent is extended or adjusted under 35 U.S.C. 154(b) by 1133 days.

(21) Appl. No.: 11/628,120

(22) PCT Filed: Jun. 2, 2005

(86) PCT No.: PCT/FR2005/001356
§ 371 (c)(1),
(2), (4) Date: Dec. 21, 2006

(87) PCT Pub. No.: WO2006/000693
PCT Pub. Date: Jan. 5, 2006

(65) Prior Publication Data
US 2009/0104595 A1      Apr. 23, 2009

(30) Foreign Application Priority Data
Jun. 2, 2004   (FR) ...................................... 04 05945

(51) Int. Cl.
*A61K 39/21*   (2006.01)
*C12Q 1/70*    (2006.01)
*C12P 21/06*   (2006.01)

(52) U.S. Cl. ......................... 435/5; 424/208.1; 435/69.1
(58) Field of Classification Search ........................ None
See application file for complete search history.

(56) References Cited

U.S. PATENT DOCUMENTS
5,413,914 A * 5/1995 Franzusoff ...................... 435/23

FOREIGN PATENT DOCUMENTS
FR        2 729 973        8/1996

OTHER PUBLICATIONS

Hertogs et al. A Rapid Method for Simultaneous Detection of Phenotypic Resistance to Inhibitors of Protease and Reverse Transcriptase in Recombinant Human Immunodeficiency Virus Type 1 Isolates from Patients Treated with Antiretroviral Drugs. Antimicrobial Agents and Chemotherapy, Feb. 1998, vol. 42, No. 2, p. 269-276.*
M'Barek et al. HIV-2 Protease resistance defined in yeast cells. Retrovirology 2006, vol. 3, p. 58-66.*
Gustchina et al. Comparative Analysis of the Sequences and Structures of HIV-1 and HIV-2 Proteases. Proteins 1991, vol. 10, p. 325-339.*
Loffert et al. PCR optimization: primer design. QIAGEN News, 1997, Issue No. 5, p. 1 and 4-6.*
Blanco, R., et al., 2003, Cell killing by HIV-1 protease, J. Biol. Chem. 278(2):1086-1093.*
Pieniazek, D et al 2004, HIV-2 protease sequences of subtypes A and B harbor multiple mutations associated with protease inhibitor resistance in HIV-1, AIDS 18:495-502.*
Liu, H., et al., 1992, Construction of a GAL1-regulated yeast cDNA expression library and its application to the identification of genes whose overexpression causes lethality in yeast, Genetics 132:665-673.*
Blanco, R., et al., 2003, Cell killing by HIV-1 protease. J. Biol. Chem. 278(2):1086-1093.*
M/Barek, N. B., et al., 2006, HIV-2 protease resistance defined in yeast cells. Retrovirol. 3(58):1-9.*
Tomasselli, A. G., et al., 1991, Actin, troponin C, alzheimer amyloid precursor protein and pro-interleukin 1 beta as substrates of the protease from human immunodeficiency virus. J. Biol. Chem. 266(22):14548-14553.*
Blanco Raquel et al., "Cell Killing by HIV-1 Protease," J. of Biol. Chem., vol. 278, Issue 2, Jan. 10, 2003, pp. 1086-1093 (Abstract Only).
Liu Haoping et al., "Construction of a GAL1-Regulated Yeast cDNA Expression Library and Its Application to the Identification of Genes Whose Overexpression Causes Lethality in Yeast," Genetics Society of America, vol. 132, No. 3, 1992, pp. 665-673.
Angel Barco et al., "Poliovirus 2A-Pro-Expression Inhibits Growth of Yeast Cells," FEBS Letters, vol. 371, 1995, pp. 4-8.
M. G. Murray et al., "Inactivation of a Yeast Transactivator by the Fused HIV-1 Proteinase: a Simple Assay for Inhibitors of the Viral Enzyme Activity," Gene, Elsevier Biomedical Press, Amsterdam, NL, vol. 134, No. 1, 1993, pp. 123-128 (Abstract Only).
Adjorlolo-Johnson, G. et al., "Prospective Comparison of Mother-to-Child Transmission of HIV-1 and HIV-2 in Abidjan, Ivory Coast," *JAMA*, Aug. 10, 1994; vol. 272, No. 6, pp. 462-466.
Ancelle, R. et al., "Long Incubation Period for HIV-2 Infection," *The Lancet*, Mar. 21, 1987, pp. 688-689.
Andersson, S. et al., "Plasma Viral Load in HIV-1 and HIV-2 Singly and Dually Infected Individuals in Guinea-Bissau, West Africa: Significantly Lower Plasma Virus Set Point in HIV-2 Infection Than in HIV-1 Infection," *Arch. Intern. Med.*, Nov. 27, 2000, vol. 160, pp. 3286-3293.
Boross, P. et al., "Effect of Substrate Residues on the P2' Preference of Retroviral Proteinases," *Eur. J. Biochem.*, 1999, vol. 264, pp. 921-929.
Büttner, J. et al., "Screening of Inhibitors of HIV-1 Protease Using an *Escherichia coli* Cell Assay," *Biochemical and Biophysical Research Communications*, 1997, vol. 233, No. 1, pp. 36-38.
Clavel, F. et al., "Isolation of a New Human Retrovirus from West African Patients with AIDS," *Science*, Jul. 18, 1986, vol. 233, pp. 343-346.

(Continued)

Primary Examiner — Jeffrey Parkin
(74) Attorney, Agent, or Firm — DLA Piper LLP (US)

(57) ABSTRACT

A method for determining sensitivity or resistance of isolates of HIV (human immunodeficiency virus) retroviruses to chemical molecules having an inhibiting activity on a viral protease or to therapeutic treatments based on inhibitors of the viral protease, including causing cell lysis of at least one yeast by expression of the retrovirus protease.

8 Claims, 2 Drawing Sheets

OTHER PUBLICATIONS

Clavel, F. et al., "Molecular Cloning and Polymorphism of the Human Immune Deficiency Virus Type 2," *Nature*, Dec. 1986, vol. 324, pp. 691-695.

Langley, C.L. et al., "HIV-1, HIV-2, Human Papillomavirus Infection and Cervical Neoplasia in High-Risk African Women," *AIDS*, 1996, vol. 10, No. 4, pp. 413-417.

Marlink, R. et al., "Reduced Rate of Disease Development After HIV-2 Infection as Compared to HIV-1," *Science*, Sep. 9, 1994, vol. 265, No. 5178, pp. 1587-1590.

Marlink, R., "Lessons from the Second AIDS Virus, HIV-2," *AIDS*, 1996, vol. 10, pp. 689-699.

Moody, M.D et al., "A Side Chain at Position 48 of the Human Immunodeficiency Virus Type-1 Protease Flap Provides an Additional Specificity Determinant," *Virology*, 1995, vol. 207, pp. 475-485.

Oroszlan, S. et al., "Retroviral Proteinases," *Current Topics in Microbiology and Immunology*, 1990, vol. 157, pp. 153-185.

Palella, F.J. et al., "Declining Morbidity and Mortality among Patients with Advanced Human Immunodeficiency Virus Infection," *The New England Journal of Medicine*, Mar. 26, 1998, vol. 338, No. 13, pp. 853-860.

Pettit, S.C. et al., "Analysis of Retroviral Protease Cleavage Sites Reveals Two Types of Cleavage Sites and the Structural Requirements of the P1 Amino Acid," *The Journal of Biological Chemistry*, Aug. 5, 1991, vol. 266, No. 22, pp. 14539-14547.

Pettit, S.C. et al., "The p2 Domain of Human Immunodeficiency Virus Type 1 Gag Regulates Sequential Proteolytic Processing and Is Required to Produce Fully Infectious Virions," *Journal of Virology*, Dec. 1994, vol. 68, No. 22, pp. 8017-8027.

Popper, S. J. et al., "Lower Human Immunodeficiency Virus (HIV) Type 2 Viral Load Reflects the Difference in Pathogenicity of HIV-1 and HIV-2," *The Journal of Infectious Diseases*, Oct. 1999, vol. 180, pp. 1116-1121.

Poulsen, A-G. et al., "Prevalence of and Mortality from Human Immunodeficiency Virus Type 2 in Bissau, West Africa," *The Lancet*, Apr. 15, 1989, pp. 827-830.

Soriano, V. et al., "Human Immunodeficiency Virus Type 2 (HIV-2) in Portugal: Clinical Spectrum, Circulating Subtypes, Virus Isolation, and Plasma Viral Load," *Journal of Medical Virology*, 2000, vol. 61, pp. 111-116.

Vittinghoff, E. et al., "Combination Antiretroviral Therapy and Recent Declines in AIDS Incidence and Mortality," *The Journal of Infectious Diseases*, 1999, vol. 179, pp. 717-720.

Wilkins, A. et al., "The Epidemiology of HIV Infection in a Rural Area of Guinea-Bissau," *AIDS*, 1993, vol, 7, No. 8, pp. 1119-1122.

* cited by examiner

US 7,989,161 B2

SEQUENCE LISTING

```
<160> NUMBER OF SEQ ID NOS: 10

<210> SEQ ID NO 1
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
ggatccggag acaccataca gggagccacc aacagcggcc gcagtagagc caataaaaat      60
aatgctaaag cgagctc                                                    77

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gaaagaagcc ccgcaacttc                                                 20
```

```
<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gggatccatg tcacttgcca                                               20

<210> SEQ ID NO 4
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cgaggatccg gagacaccat acagggagcc accaacagcg gccgcgccat gcctcaattc   60

<210> SEQ ID NO 5
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gcggagctcg ctttagcatt attttttattg gctctactgc ggccgcttaa gatt        54

<210> SEQ ID NO 6
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cgaggatccg gagacaccat acagggagcc accaacagcg gccgcgccat gcctcaattc   60

<210> SEQ ID NO 7
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gcggagctcg ctttagcatt attttttattg gctctactgc ggccgcttaa gatt        54

<210> SEQ ID NO 8
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
ggatccggag acaccataca gggagccacc aacagcggcc                         40
```

-continued

```
<210> SEQ ID NO 9
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
gcagtagagc caataaaaat aatgctaaag cgagctc                          37

<210> SEQ ID NO 10
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gcggagctcg ctttagcatt atttttattg gctactgcgg ccgcttaaga tt         52
```

METHODS FOR DETERMINING HUMAN IMMUNODEFICIENCY VIRUS TYPE 2 (HIV-2) PROTEASE SENSITIVITY OR RESISTANCE TO ANTIVIRALS UTILIZING AN INDUCIBLE YEAST EXPRESSION SYSTEM

RELATED APPLICATION

This is a §371 of International Application No. PCT/FR2005/001356, with an international filing date of Jun. 2, 2005 (WO 2006/000693 A1, published Jan. 5, 2006), which is based on French Patent Application No. 04/05945, filed Jun. 2, 2004.

TECHNICAL FIELD

This disclosure relates to methods for determining the sensitivity or resistance of retroviruses such as HIV to therapeutic treatments based on viral protease inhibitors, by the use of yeast, particularly to the use of yeast for determining the resistance or sensitivity of the viral protease to the chemical molecules used in the context of therapeutic protocols. The disclosure also relates to diagnostic kits comprising the elements for implementing the method.

BACKGROUND

The aetiological agents of AIDS are the human immunodeficiency viruses types 1 and 2. These viruses, which share certain clinical and biological characteristics, have major differences, in particular with regard to the ways in which the host is infected. Infection by HIV-2 is more difficult than by HIV-1 (Ancelle R, O Bletry, A C Baglin, F Brun-Vezinet, M A Rey and P Godeau, 1987, *Long incubation period for HIV-2 infection*. Lancet. 1:688-9; Marlink R, P Kandki, I Thior, K Travers, G Eisen, T Siby, I Traore, C C Hsieh, M C Dia and E H Gueye. 1994. *Reduced rate of disease development after HIV-2 infection as compared to HIV-1*. Science. 265:1587-90; Adjorlolo-Johnson G, K M De Cock, E Ekpini, K M Vetter, T Sibailly, K Brattegaard, D Yavo, R Doorly, J P Whitaker and L Kestens. 1994. *Prospective comparison of mother-to-child transmission of HIV-1 and HIV-2 in Abidjan, Ivory Coast*. JAMA. 272:462-6; Marlink, R. 1996. *Lessons from the second AIDS virus, HIV-2*. AIDS. 10:689-99.), the plasma viral load of individuals infected by HIV-2 is less high than that in individuals infected by HIV-1 (Andersson S, H Norrgren, Z da Silva, A Biague, S Bamba, S Kwok, C Christopherson, G Biberfeld, and J Albert. 2000. *Plasma viral load in HIV-1 and HIV-2 singly and dually infected individuals in Guinea-Bissau, West Africa: significantly lower plasma virus set point in HIV-2 infection than in HIV-1 infection*. Arch. Intern. Med. 160:3286-93; Popper S J, A D Sarr, K U Travers, A Gueye-Ndiaye, S Mboup, M E Essex, and P J Kanki. 1999. *Lower human immunodeficiency virus (HIV) type 2 viral load reflects the difference in pathogenicity of HIV-1 and HIV-2*. J Infect Dis. 180:1116-21.), and the individuals infected by HIV-2 develop the illness more slowly (Vittinghoff E, S Scheer, P O'Malley, G Colfax, S D Holmberg and S P Buchbinder. 1999. *Combination antiretroviral therapy and recent declines in AIDS incidence and mortality*. J Infect Dis. 179: 717-20; Blanco R, Carrasco, L, and Ventoso, I. 2003. *Cell killing by HIV-1 protease*. J. Biol. Chem. 278:1086-93; Liu H, Krizek J, and Bretscher A. 1992. *Construction of a GAL1-regulated yeast cDNA expression library and its application to the identification of genes whose overexpression causes lethality in yeast*. Genetics 132:665-673).

HIV-2 was identified for the first time in West Africa in 1986 (Clavel F, D Guetard, F Brun-Vezinet, S Chamaret, M A Rey, M O Santos-Ferreira, A G Laurent, C Dauguet, C Katlama, and C Rouzioux. 1986. *Isolation of a new human retrovirus from West African patients with AIDS*. Science. 233: 343-6). In this region, the prevalence of HIV-2 varies between 1% and 10% (Langley C L, E Benga-De, C W Critchlow, I Ndoye, M D Mbengue-Ly, J Kuypers, G Woto-Gaye, S Mboup, C Bergeron, K K Holmes, and N B Kiviat. 1996. *HIV-1, HIV-2, human papillomavirus infection and cervical neoplasia in high-risk African women*. AIDS. 10:413-7, Poulsen A G, B Kvinesdal, P Aaby, K Molbak, K Frederiksen, F Dias and E Lauritzen. 1989. *Prevalence of and mortality from human immunodeficiency virus type 2 in Bissau, West Africa*. Lancet. 1:827-31; Wilkins A, D Ricard, J Todd, H Whittle, F Dias, and A Paulo Da Silva. 1993. *The epidemiology of HIV infection in a rural area of Guinea-Bissau*. AIDS. 7:1119-22). The majority of these cases of infection by HIV-2, outside West Africa, are found in European countries and especially in Portugal where the individuals infected by VIH-2 represent 13% of the population infected by human immunodeficiency viruses (Soriano V, P Gomes, W Heneine, A Holguin, M Doruana, R Antunes, K Mansinho, W M Switzer, C Araujo, V Shanmugam, H Lourenco, J Gonzalez-Lahoz and F Antunes. 2000. *Human immunodeficiency virus type 2 (HIV-2) in Portugal: clinical spectrum, circulating subtypes, virus isolation, and plasma viral load*. J Med. Virol. 61:111-6). In France it has been estimated that 1% of the population infected by HIV is infected by the type 2 virus.

In developed countries, the individuals infected by HIV-1 and/or by HIV-2 are treated by chemical therapy, composed of molecules having an inhibiting activity for one or other of the two viral enzymes: Reverse Transcriptase and Protease.

Although this treatment has significantly helped to reduce morbidity and mortality caused by HIV infection (Palella F J, Jr, K M Delaney, A C Moorman, M O Loveless, J Fuhrer, G A Satten, D J Aschman and S D Holmberg. 1998. *Declining morbidity and mortality among patients with advanced human immunodeficiency virus infection. HIV Outpatient Study Investigators*. N. Engl. J. Med. 338:853-60; Vittinghoff E, S Scheer, P O'Malley, G Colfax, S D Holmberg and S P Buchbinder. 1999. *Combination antiretroviral therapy and recent declines in AIDs incidence and mortality*. J. Infect. Dis. 179:717-20), some cases of therapeutic failure have been observed.

The possibility of amplifying, from the plasma RNA or cell DNA of the individuals infected by HIV-1 and in therapeutic failure, has made it possible to understand at the molecular level the spontaneous or progressive inefficacy of therapeutic treatments. The determination in particular of the nucleic sequence of the two viral enzymes Reverse Transcriptase and Protease has shown the appearance of a certain number of mutations. The results obtained during studies in vitro, in which a wild viral strain (and therefore sensitive to treatments) carried the said mutations, have clearly demonstrated the implication of these mutations in the resistance of the virus to treatment.

Researchers have therefore done a certain amount of work on these mutations and on the resistances that they generate, in order to orient and guide the choice of therapeutic treatment and to optimize its efficacy.

Unfortunately, the economic strategies of the laboratories have the majority of the time led to a general lack of interest in the scientific community with regard to the treatment of patients infected by HIV-2 (the populations most affected by HIV-2 being mainly those in developing countries) or have led to unsuitable solutions: treatments, tests and analyses that are too expensive, diagnoses that are too lengthy or impossible to implement on site, absence of competent structures in the country concerned, etc.

Thus the results obtained during the various studies carried out on HIV-2 have not been sufficiently consistent to make it possible to formulate a correlation between a particular mutation of the HIV-2 protease, and a resistance phenotype.

In addition, the progression of the illness being slower in individuals infected by HIV-2 than in those infected by HIV-1, the counting of T CD4 cells and the determination of the plasma viral load do not rapidly take account of the emergence of resistant strains in patients under treatment.

There exist at the present time three companies that provide the resistance profile of an HIV strain isolated from an infected patient. Conceptionally the three tests resemble each other and are based on the ability of each protease inhibitor to inhibit the release of an infectious recombinant virus comprising the protease of the virus infecting the patient. The companies are: Viralliance (France), which produces Phenoscript™, Virco (Belgium), which produces Antivirogram™, and Virologic (United States), which produces Phenosense™. In the three cases, performing these tests requires significant logistic organisation, personnel skilled in molecular biology and virology, and expensive infrastructures of the P3 secure laboratory type (it would appear that a complete profile would currently cost between 800 and 1,000 euros per sample). The delay existing between the time when the biological material arrives at the laboratories and the time when the resistance profile is established varies, for each strain of HIV-1, between two and three weeks.

Under these circumstances, putting on the market a reliable rapid test that is simple to implement and inexpensive would be advantageous. Such a test would assist the treating doctors to monitor the appearance of resistant strains in patients infected by retroviruses, in particular HIV 1 or 2, in particular for deprived populations. Moreover, this test could also be used for a "high speed" research for new molecules having inhibiting activity for the retrovirus protease.

SUMMARY

This disclosure relates to a method for determining sensitivity or resistance of isolates of HIV (human immunodeficiency virus) retroviruses to chemical molecules having an inhibiting activity on a viral protease or to therapeutic treatments based on inhibitors of the viral protease, including causing cell lysis of at least one yeast by expression of the retrovirus protease.

This disclosure also relates to a method for determining sensitivity or resistance of isolates of HIV (human immunodeficiency virus) retroviruses to chemical molecules having an inhibiting activity on a viral protease or to therapeutic treatments based on inhibitors of the viral protease, including extracting nucleic acids (DNA or RNA) from cells (blood or other) taken from a person or animal infected by the retrovirus; amplifying sequences coding for the protease of the retrovirus to be studied, with or without the or some of the amino acid sequences situated upstream and downstream of the cleavage site of the precursor in which they are situated; recombining the fragments of DNA, the final product of the amplification, and an expression vector allowing the expression of the sequence coding for the protease of the retrovirus to be studied under the control of a known inducible promoter, and co-transformation of the recombined vector with at least one yeast cell whose cell lysis is caused by expression of the retrovirus protease; culturing the co-transformed yeast cell or cells to obtain a sufficient number of transformants to perform the sensitivity or resistance test, and recovery of the transformants issuing from the co-transformed cell, on any suitable medium; incubating the transformants in the presence of an increasing concentration of each viral protease inhibitor to be tested; counting the living cells; and deducing the resistance phenotype.

This disclosure further relates to a diagnostic kit including nucleotide primers including, for a first amplification, primers: sense primer: 5' GAAAGAAGCCCCGCAACTTC3' (SEQ ID NO:2) and antisense primer: 5'GGGATCCATGT-CACTTGCCA3' (SEQ ID NO:3) and, for a second amplification, primers: sense primer: 5'CGAGGATCCGGAGA-CACCATACAGGG AGCCACCAACAGCGGCCGCGCCATGCCTCAATTC3' (SEQ ID NO:4) and antisense primer: 5'GCG-GAGCTCGCTTTAGCATTATTTTTATTG-GCTCTACTGCGGCCGCTTAAGATT3' (SEQ ID NO:5); at least one expression vector; at least one strain of yeast with an auxotrophy marker to permit selection of a transformant expressing a viral protease; and at least one multi-well plate or any other suitable support.

DETAILED DESCRIPTION

Figure 1:
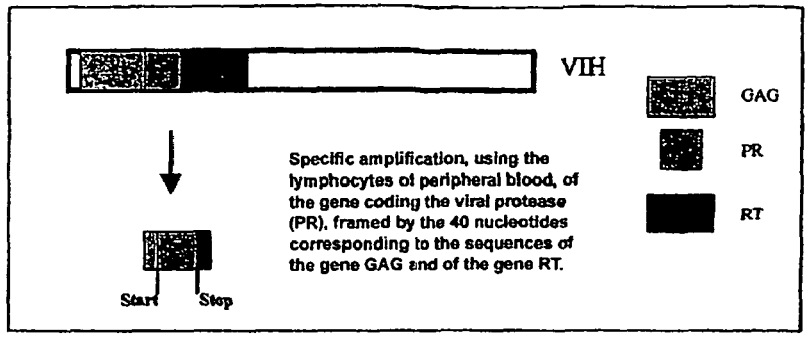
FIGS. 1 and 2 are schematic representations of the co-transformation of the pRS316-Gal1/10M vector cleaved by the Not1 restriction enzyme with the product of the second PCR to obtain a transformed yeast cell having the sequence of the HIV-2 protease under the control of the inducible promoter Gal1.

Our methods and kits permit the rapid and low-cost definition of the resistance phenotype of the HIV-2 protease in infected patients, by virtue of the use of yeast.

Our methods can also be implemented to define the resistance phenotype of the HIV-1 protease, or the protease of any other retrovirus.

A scientific article that appeared in 2003 demonstrated that the expression of the HIV-1 protease by the yeast *Saccharomyces cerevisiae* caused the death of the latter through a still unknown mechanism, the consequence of which was the cell lysis of the yeast in question (Blanco R, Carrasco L and Ventoso I. 2003. Cell killing by HIV-1 protease. J. Biol. Chem. 278:1086-93).

We demonstrated that the same phenomenon occurred when the yeasts expressed the HIV-2 protease. Consequently, by inhibiting the viral enzymatic activity by modification of its catalytic site, we succeeded in preventing the appearance of this cell event.

In addition, Blanco et al (Blanco R, Carrasco L, and Ventoso I. 2003. Cell killing by HIV-1 protease. J. Biol. Chem. 278:1086-93) also showed that the inhibition of the HIV-1 protease by one of the inhibitors used in anti-HIV therapy inhibited the cell death of the yeast caused by the expression of the viral protease. Because of this fact, it is possible to quantitatively measure the sensitivity and resistance of the protease of infected individuals to the various inhibitor molecules.

Our methods, therefore, make it possible to determine in the cellular context of the yeast, the sensitivity phenotype of the viral protease of a retrovirus such as HIV-2, to drugs with an inhibiting activity.

In other words, it is possible to determine the sensitivity or resistance of isolates of retroviruses such as HIV (human immunodeficiency virus) to chemical molecules having an inhibiting activity on the viral protease or to therapeutic treatments based on inhibitors of the viral protease, characterized by the use for this purpose of at least one yeast whose cell lysis is caused by the expression of the retrovirus protease.

The method comprises an expression vector, the choice of the cell system, the method of expressing proteases of infected individuals and the test of susceptibility to drugs.

It comprises the following steps:
extracting the nucleic acids (DNA or RNA) from cells (blood or other) taken from the individual or animal infected by the retrovirus, by any suitable means;
amplifying the sequences coding for the protease of the retrovirus to be studied;
recombining the fragments of DNA, the final product of the amplification, and an expression vector allowing the expression of the sequence coding for the protease of the retrovirus to be studied under the control of a known inducible promoter, and co-transformation of the recombined vector with at least one yeast cell whose cell lysis is caused by the expression of the retrovirus protease;
culture of the co-transformed yeast cell or cells to obtain a sufficient number of transformants to perform the sensitivity or resistance test, and recovery of the transformants issuing from the co-transformed cell, on any suitable medium;
incubation of the transformants in the presence of an increasing concentration of each viral protease inhibitor to be tested;
counting the living cells; and
deducing the resistance phenotype.

The sequences coding the therapeutic targets (reverse transcriptase and protease), as well as the so-called "structure proteins" (matrix, capsid, nucleocapsid) and the Integrase enzymatic activity, are situated within a common polypeptide precursor called Gag-Pol, coded by the gag-pol viral gene (Clavel F, Guyader M, Guetard D, Salle M, Montagnier L, Alizon M. 1986. Molecular cloning and polymorphism of the human immune deficiency virus type 2. Nature, 324:691-5). It is the action of the viral protease that, by hydrolysis of specific peptide bonds referred to as cleavage sites, framing the primary sequences of the various constituents of the precursor, is responsible for the release of these proteins (Oroszlan S and Luftig R B. 1990. Retroviral proteinases. Curr Top Microbiol Immunol. 157:153-85. It has been shown that, for the HIV-1 protease, the amino acid sequences are situated upstream and downstream of the cleavage site fulfilling an important role in the recognition event of the enzyme for its substrate, and therefore determinant for its proteolytic activity (Pettit S C, Simsic J, Loeb D D, Everitt L, Hutchison C A 3rd, Swanstrom R. 1991. Analysis of retroviral protease cleavage sites reveals two types of cleavage sites and the structural requirements of the P1 amino acid. J. Biol. Chem. 266:14539-47, Pettit S C, Moody M D, Wehbie R S, Kaplan A H, Nantermet P V, Klein C A, Swanstrom R. 1994. The p2 domain of human immunodeficiency virus type 1 Gag regulates sequential proteolytic processing and is required to produce fully infectious virions. J Virol. 68:8017-27, Moody M D, Pettit S C, Shao W, Everitt L, Loeb D D, Hutchison C A 3rd, Swanstrom R. 1995. A side chain at position 48 of the human immunodeficiency virus type-1 protease flap provides an additional specificity determinant. Virology. 207:475-85, Boross P, Bagossi P, Copeland T D, Oroszlan S, Louis J M, Tozser J. 1999. Effect of substrate residues on the P2' preference of retroviral proteinases. Eur J Biochem. 264:921-9.).

The sequences of the protease amplified by the method include those coding for the isolated protein or those coding for the protein and comprising all or some of the amino acid sequences situated upstream and downstream of the cleavage site of the protein precursor in which they are situated.

The protocols used in the laboratory to obtain yeast transformants coding for an exogenous gene generally begin with a first step for obtaining fragments of DNA coding for the gene of interest, gene amplification (PCR technique) or release of the gene by virtue of the action of the restriction enzymes which cut DNAs containing the sequence of interest. This first step can be equivalent in time to half a day's work.

The DNA fragment released is then sub-cloned in an expression vector by the action of the DNA Ligase enzyme (an operation lasting one night) and the product of the reaction is amplified in a bacterium, after its transformation (one day to obtain bacteria having incorporated plasmid DNA, and one and a half days of obtaining and characterising the transformant sought, containing the plasmid coding for the gene of interest).

Moreover, to produce sufficient quantities of the plasmid containing the gene of interest with a view to transformation of the yeast, the bacterial clone obtained in the previous step was amplified (one night) and the plasmids were purified by conventional known methods (one day).

The purified plasmid obtained is then used to transform the selected yeast strain (½ day).

The transformed yeast strain is obtained approximately 4 days after the transformation event.

Consequently, by using conventional protocols making it possible to obtain a sufficient quantity of yeast transformants for a subsequent study of a gene of interest, for example for developing a sensitivity or resistance test, the time that elapses between the preparation of the DNA fragment coding for the gene of interest and the obtaining of the yeast strain expressing it is a minimum of 8 days. Moreover, as disclosed above, several techniques must be used.

The magnitude of these delays and the multiplicity of the techniques used necessarily give rise to high production costs, incompatible with the development of a rapid sensitivity or resistance test that is simple to implement and inexpensive.

We therefore developed of an innovative technology allowing easy management of a large number of samples, for the purpose in particular of testing, rapidly, effectively and at less cost, a large quantity of proteases issuing from different patients under treatment.

Considering the studies on the ability of yeast to repair "broken DNA" (nicked DNA) by the homologous recombination mechanism, it was found that, during this cell event, a DNA molecule is repaired at a precise point in its sequence, by putting in place homologous sequences at the "nicking" site and taken within another DNA molecule. By using this physiological phenomenon, it is possible to introduce a defined sequence within the "nicked" DNA provided that the defined sequence is framed on each side by sequences identical to those situated around the "nicking" site.

The minimum size of the homologous sequences that have to be present in the two DNA molecules for the recombination event to be able to take place is approximately 40 pairs of bases.

This technique very advantageously simplifies obtaining the transformants by reducing in particular the number of manipulations which involve a significant reduction in the experimentation time necessary (approximately half compared with the known protocols) and in the production cost.

Use of this technique also enables a large number of samples to be manipulated at the same time.

EXAMPLE

This example of implementation is used for preference when the protease expressed is the isolated protein. When the protease is expressed with all or some of the amino acid sequences situated upstream and downstream of the cleavage site of the protein precursor that contains it, the primers and nucleotide fragments disclosed above will be modified accordingly.

1—Preparation and Modification of the Expression Vector:

The modification enables the ability to sub-clone the gene of the protease of each individual studied and to transform the yeast with the plasma obtained by a simple and rapid procedure (a single-step procedure).

We created a modified version of the vector pRS316-Gal1/10, which comprises the inducible promoter GAL1/10 in position 5' of the cloning site of the gene to be expressed (Liu H, Krizek J, and Bretscher A. 1992. *Construction of a GAL-1 regulated yeast cDNA expression library and its application to the identification of genes whose overexpression causes lethality in yeast. Genetics* 132:665-673).

Because of this, the gene is expressed when the cell is transformed with this vector and grow in the presence of galactose and the gene is not expressed when the cells transformed are in the presence of glucose as a carbon source.

For the fragment of amplified viral DNA to be able to be inserted by homologous recombination in the expression vector, the vector must be modified by adding to it, just after the sequence of the inducible promoter, a primer 5' of approximately 40 pairs of bases, followed by a single restriction site (in order to be able to linearize the vector), and a primer 3' of approximately 40 pairs of bases. Although this modified and linearized vector is a good substrate for the homologous recombination event, the sequence introduced at position 5' (between the gene and the promoter) must not inhibit the transcription of the genes.

To produce the modified version of the expression vector pRS316-Gal 1/10, we exchanged the BamHI-Sac1 fragment of this site with another DNA fragment also framed by the BamHI-Sac1 restriction sites that contain (from 5' to 3'):
 the BamHI restriction site, unique in the vector, followed by
 the 35 to 45 nucleotides in the HIV-2 sequence situated just upstream of the protease, followed by
 an Not1 restriction site, unique in the vector, followed by
 the 35 to 45 nucleotides of the HIV-2 sequence situated just downstream of the protease, followed by
 the Sac1 restriction site, unique in the vector.

Modifications to the size of this fragment of approximately 80-90 pairs of bases were carried out in order to optimize the experimental cloning, transformation and expression system. A single modified fragment amongst 10 different ones that were tested was sufficiently optimum for the homologous recombination and for the expression of the viral protease.

The sequence of this fragment is as follows:

5'GGATCCGGAGACACCATACAGGGAGCCACCAACAGCGGCCGCAGTAGA

GCCAATAAAAATAATGCTAAAGCGAGCTC3'

The pRS316-Gal1/10 expression vector thus modified is called pRS316-Gal1/10M.

2—Choice of the Cell System

Any strain of yeast with auxotrophy markers necessary in order to allow the selection of the transformant expressing the viral protease, and preferably any strain of *Saccharomyces cerevisiae*.

3—Sub-cloning of the Proteases of Individuals Affected by the Retrovirus, and Transformation of Yeasts in a Single Step The DNA sequence coding the HIV-2 protease is amplified by the PCR technique, twice.

The object of the first is to produce a significant quantity of DNA. This reaction takes place using DNA extracted from lymphocytes of the peripheral blood of infected individuals. The nucleotide primers used are of the type:

```
Sense primer:
5'GAAAGAAGCCCCGCAACTTC3'

Antisense primer:
5'GGGATCCATGTCACTTGCCA3'.
```

The object of the second amplification is to frame the protease of an initialisation codon of the transcription (ATG) and of a termination codon of the transcription (TAA) and to add on each side the sequences of approximately 40 nucleotides that we brought to the vector when it was modified. This PCR reaction takes place on the product of the first PCR with the primers of the type:

```
Sense primer:
5'CGAGGATCCGGAGACACCATACAGGGAGCCACCAACAGCGGCCGCGCC

ATGCCTCAATTC3'

Antisense primer:
5'GCGGAGCTCGCTTTAGCATTATTTTTATTGGCTCTACTGCGGCCGCTT

AA GATT3'.
```

The isolated protease or its cleavable precursor protein is flanked by initiation and termination codons.

Figure 2:
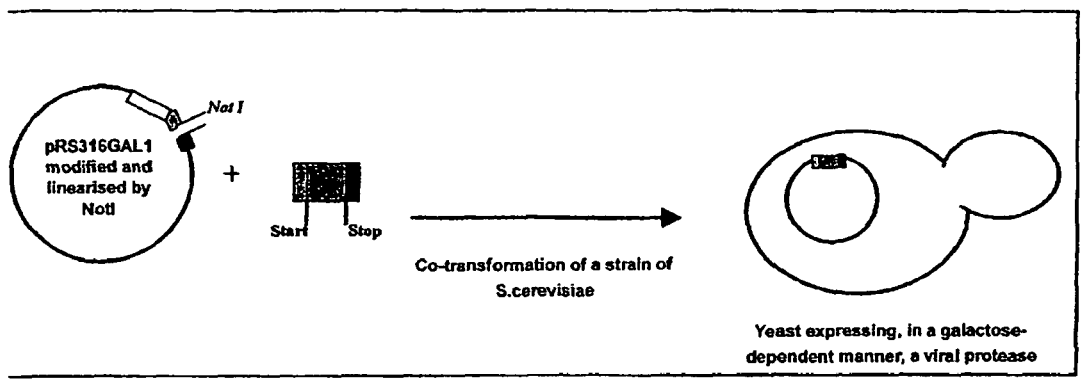

The co-transformation of the pRS316-Gal1/10M vector cleaved by the Not1 restriction enzyme with the product of the second PCR makes it possible, through the homogeneous recombination event that took place in the cell, to obtain a transformed yeast cell, carrying the sequence of the HIV-2 protease under the control of the inducible promoter Gal (FIGS. 1 and 2).

4—The Test

A sample of peripheral blood is taken from the individual infected with HIV-2. The lymphocytes issuing from this sampling are purified or not, and their DNA extracted by known methods.

This DNA undergoes the two aforementioned PCR reactions in order to create the fragment of DNA, carrying the sequence of the protease with or without the or some of the amino-acid sequences situated upstream and downstream of the cleavage site of the precursor in which it is situated, and compatible with the expression vector in order to cause the phenomenon of homologous recombination in the transformed cells.

After purification of the product of the second PCR a yeast strain having a genotype ura3 is co-transformed with the pRS316Gal1/10M linear vector (by its Not1 site).

The transformants potentially producing the protease are recovered on any suitable carrier, such as for example gelose composed of agar, glucose as a source of carbon, and a synthetic environment with a deficiency of uracil.

Approximately $10^5$ cells, issuing from a single transformant, are deposited and distributed in 12 wells with a 96-well plate, and incubated in galactose in the presence of 11 increasing concentrations of each inhibitor to be tested. The twelfth well does not contain any inhibitor.

Figure 3:
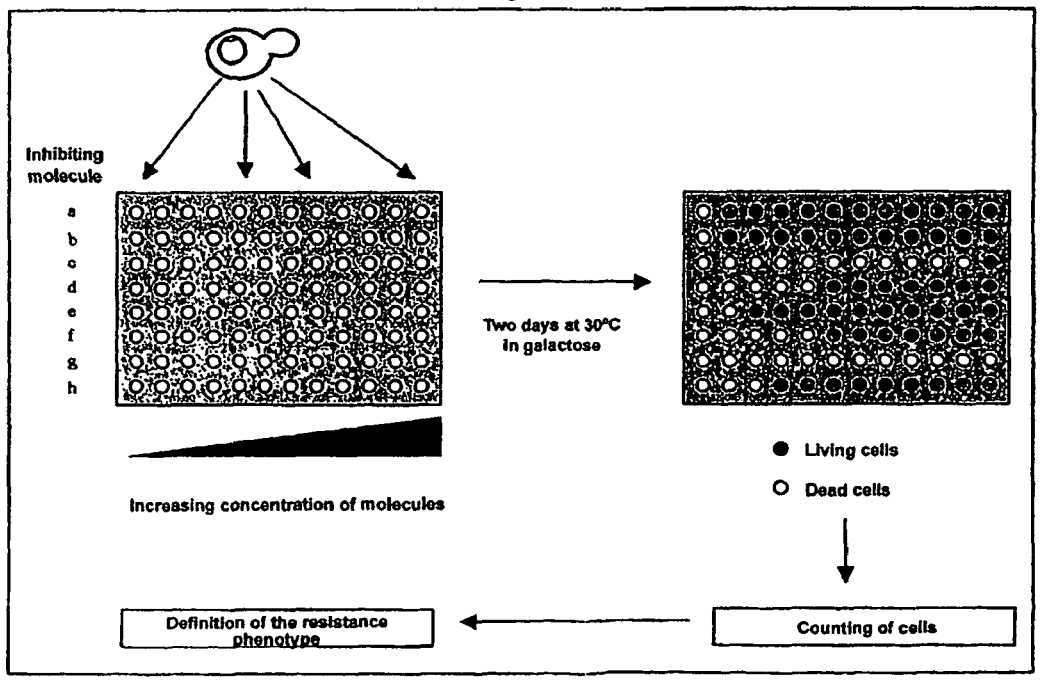
FIG. 3 is a schematic representation of the counting of living and dead cells and a determination of the phenotype.

After 36-48 hours at 30° C., the living cells are counted by a densitometric reading at 600 nm (FIG. 3).

The dose necessary for inhibiting half the cell growth under these conditions, compared with the cell growth in the absence of drugs and in the presence of glucose ($IC_{50}$), defines the susceptibility or resistance of this specific strain.

The interval of time between the blood sampling and the definition of the resistance profile is only one week.

Diagnostic Kit for Resistance to Retroviruses

A diagnostic kit for determining the sensitivity or resistance of retrovirus isolates to therapeutic retroviral treatments based on inhibitors of the viral protease, comprising:

nucleotide primers, and for example nucleotide primers as previously disclosed for implementation of the amplification of DNA coding for the retrovirus protease by the PCR technique, namely:

for the first amplification primers of the type:

```
Sense primer:        5'GAAAGAAGCCCCGCAACTTC3'

Antisense primer:    'GGGATCCATGTCACTTGCCA3'
``` for the second amplification, primers of the type:

```
Sense primer:
5'CGAGGATCCGGAGACACCATACAGGGAGCCACCAACAG CGGCCGCGC

CATGCCTCAATTC3'

Antisense primer:
5'GCGGAGCTCGCTTTAGCATTATTTTTATTGGCTCTACTGCGGCCGCTT

AA GATT3';
``` at least one expression vector and for example the plasmid modified and linearized according to the methods of the invention and as previously described;

at least one strain of yeast with the necessary auxotrophy marker in order to permit the selection of the transformant expressing the viral protease, and preferably a strain of *Saccharomyces cerevisiae*; and at least one multi-well plate or any other suitable support.

Naturally, when the amplification is carried out on the DNA coding for the protease of the retrovirus with all or some of the amino acid sequences situated upstream and downstream of the cleavage site of the protein precursor that contains it, the primers and nucleotide fragments will be modified accordingly.

Figure 4:
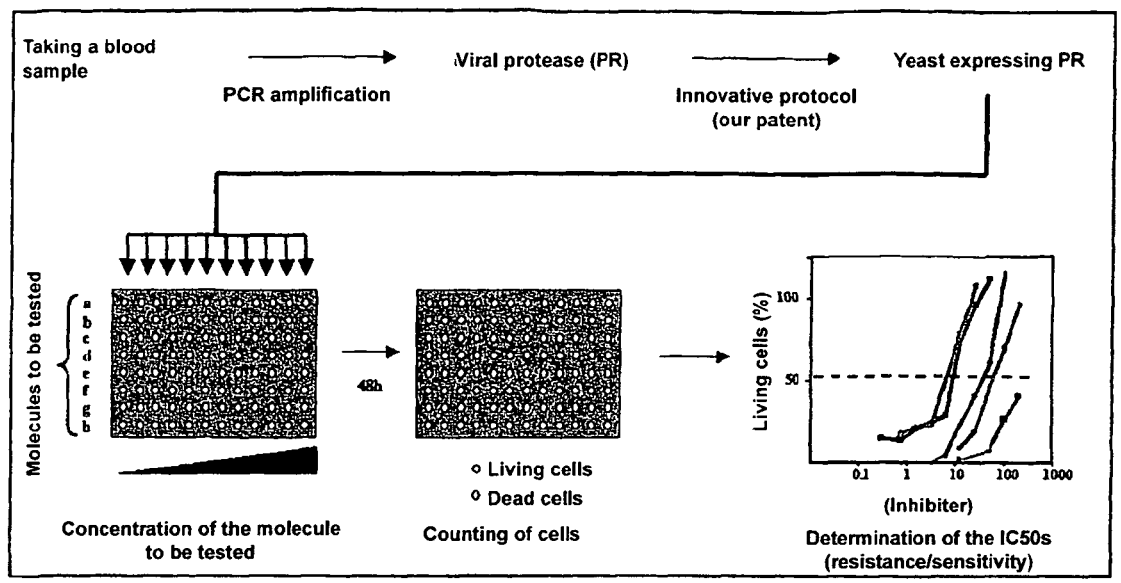
FIG. 4 is a schematic representation of a diagnostic kit.

The principle of the kit, also illustrated in FIG. 4, is as follows:

Using the blood of the patient, the gene coding for the viral protease is amplified by an RT-PCR reaction with the primers described in the method according to the invention and supplied in the kit.

Amplification of the gene of the viral protease using cell DNA is also possible.

The amplified product and the modified and linearized vector (also supplied in the kit) are used for transforming a strain of yeast, also supplied in the kit, in a multi-well plate.

In a preferred though in no way limiting fashion, after incubation at 30° in a dry oven in a selective medium containing glucose, 2 microliters of the cell suspension are transferred to a new plate, supplied in the kit, containing increasing concentrations of each active principle used in therapy. 300 microliters of the selected medium containing galactose are added to each well, before incubating at to 30° C. in a dry oven for 36-48 hours.

At the end of the incubation, the living cells are counted by a densitometric reading at 600 nm. The dose necessary for inhibiting half the cell growth, compared with the cell growth of the strain of yeast not expressing the viral protease, will define the I'$IC_{50}$ for each inhibitor. The comparison between the I'$IC_{50}$s obtained and those of a reference wild protease makes it possible to determine any resistance phenotype.

The interval of time between the taking of blood and the definition of the resistance profile is only one week.

---

The invention claimed is:

1. A method for determining if an HIV-2 retrovirus is sensitive, or resistant, to an HIV-2 viral protease inhibitor comprising:

a) extracting nucleic acids from cells taken from a human infected by a HIV-2 retrovirus;

b) amplifying from the extracted nucleic acids a nucleic acid sequence comprising the sequence encoding the amino acid sequence of HIV-2 protease;

c) combining the amplified sequence and an expression vector allowing the expression of the sequence coding of the HIV-2 protease under the control of an inducible promoter by transforming a yeast cell with said sequence and expression vector;

d) culturing the transformed yeast cell under conditions that do not result in HIV-2 protease expression to obtain a population;

e) inducing the expression of the HIV-2 protease by inducing the promoter of the expression vector;

f) incubating the population with the HIV-2 viral protease inhibitor;

g) monitoring growth of the population;

h) determining if the population grew or stopped growing; whereby the HIV-2 retrovirus is determined to be sensitive to the HIV-2 viral protease inhibitor if the population grew after incubation with said HIV-2 viral protease inhibitor, or the HIV-2 isolate is determined to be resistant to the HIV-2 viral protease inhibitor if the population stopped growing after incubation with said HIV-2 viral protease inhibitor.

2. The method of claim 1, wherein the step h) of determining if the population grew or stopped growing comprises the determination of the IC50 of the HIV-2 viral protease inhibitor.

3. The method of claim 1, wherein the nucleic acids are extracted from blood cells taken from a human infected by a HIV-2 retrovirus.

4. The method of claim 1 wherein the yeast cell is *Saccharomyces cerevisiae* cell.

5. The method of claim 1, wherein step b) comprises:

i) a first PCR amplification of the nucleic acid sequence encoding an amino acid sequence comprising an HIV-2 protease from the DNA of lymphocytes in the peripheral blood of the human infected with a HIV-2 retrovirus using:

a sense primer having the nucleic acid sequence shown in SEQ ID NO:2 and an antisense primer having the nucleic acid sequence shown in SEQ ID NO:3 to obtain a first PCR product ii) a second PCR amplification of a nucleic acid sequence from the first PCR product using:

a sense primer having the nucleic acid sequence shown in SEQ ID NO:6 and an antisense primer having the nucleic acid sequence shown in SEQ ID NO:7.

6. The method of claim 1 wherein the inducible promoter is a galactose inducible promoter.

7. The method of claim 1 wherein the expression vector is the linear plasmid pRS316-Gal1/10.

8. The method of claim 7 wherein the expression vector is a modified pRS316-Gal1/10 that comprises the inducible promoter Gal1/10 located in position 5' of the cloning site of the gene to be expressed and in which the fragment BamHT-SacI is replaced by another fragment of DNA consisting of:

a BamHI restriction site in position 5', followed by
the nucleic acid shown in SEQ ID NO:8, followed by
a NotI restriction site, followed by
the nucleic acid shown in SEQ ID NO:9, followed by
a SacI restriction site wherein the expression vector contains only a single BamHI restriction site, a single NotI restriction site and a single SacI restriction site.

* * * * *